(12) United States Patent
Flower et al.

(10) Patent No.: US 12,207,845 B2
(45) Date of Patent: Jan. 28, 2025

(54) RETRACTOR, DISTRACTOR, AND CAMERA SYSTEM FOR CERVICAL PROCEDURES

(71) Applicant: Viseon, Inc., Irvine, CA (US)

(72) Inventors: Robert J. Flower, Irvine, CA (US); Todd D. McIntyre, Irvine, CA (US); Ravut Chhit, Irvine, CA (US); Peter G. Davis, Irvine, CA (US)

(73) Assignee: Viseon, Inc., Irvine, CA (US)

( * ) Notice: Subject to any disclaimer, the term of this patent is extended or adjusted under 35 U.S.C. 154(b) by 227 days.

(21) Appl. No.: 18/064,790

(22) Filed: Dec. 12, 2022

(65) Prior Publication Data

US 2023/0109735 A1 Apr. 13, 2023

Related U.S. Application Data

(63) Continuation of application No. 17/496,648, filed on Oct. 7, 2021, now Pat. No. 11,523,846.

(60) Provisional application No. 63/089,954, filed on Oct. 9, 2020.

(51) Int. Cl.
*A61B 17/66* (2006.01)
*A61B 90/00* (2016.01)

(52) U.S. Cl.
CPC ............ *A61B 17/66* (2013.01); *A61B 90/361* (2016.02)

(58) Field of Classification Search
CPC ......... A61B 17/02; A61B 17/00; A61B 17/58; A61B 17/66; A61B 19/00; A61B 13/06; A61B 90/361
USPC ................. 606/90, 279, 86 A; 600/201, 206
See application file for complete search history.

(56) References Cited

U.S. PATENT DOCUMENTS

| | | | | |
|---|---|---|---|---|
| 5,944,658 | A * | 8/1999 | Koros | A61B 17/7077 600/231 |
| 2006/0084844 | A1* | 4/2006 | Nehls | A61B 17/1757 600/227 |
| 2010/0312069 | A1* | 12/2010 | Sutherland | A61B 17/0218 600/245 |
| 2015/0141755 | A1* | 5/2015 | Tesar | A61B 1/051 600/109 |
| 2019/0307439 | A1* | 10/2019 | Chhit | A61B 17/0206 |

* cited by examiner

Primary Examiner — Eduardo C Robert
Assistant Examiner — David C Comstock
(74) Attorney, Agent, or Firm — Crockett & Crockett, PC; K. David Crockett, Esq.

(57) ABSTRACT

A retractor, distractor, and camera system with the camera system and/or distractor configured to provide releasable attachment of the camera system to the distractor, and also provide for rotation of the camera assembly relative to the distractor to allow for adjusting the aim of the camera viewing axis to obtain an image of the surgical workspace established by the retractor.

8 Claims, 3 Drawing Sheets

US 12,207,845 B2

RETRACTOR, DISTRACTOR, AND CAMERA SYSTEM FOR CERVICAL PROCEDURES

This application is a continuation of U.S. application Ser. No. 17/496,648, filed Oct. 7, 2021, which claims priority to U.S. Provisional Application 63/089,954 filed Oct. 9, 2020.

FIELD OF THE INVENTIONS

The inventions described below relate to the field of retractor, distractor, and camera systems for spine surgery, including cervical procedures.

BACKGROUND

In some cervical spine surgeries, surgeons use a retractor to retract tissue along an incision in the front of the neck to create an opening for access to the cervical vertebrae, and use a distractor to pull vertebrae apart. For visualization, surgeons currently use a microscope. For lumbar surgery, placement of a camera at the proximal end of a retractor system has been proposed, as in Chhit, et al., Devices And Method For Access And Visualization For Lumbar Interbody Fusion (LIF), U.S. Pat. No. 10,646,212 (May 12, 2020). For cervical procedures, in addition to retractors, distractors are needed to pull adjacent vertebrae apart. Addition of a camera to the distractor combined with a display screen which the surgeon may view to guide the surgery, can provide superior visualization of the surgical workspace.

SUMMARY

The devices and methods described below provide for visualization of a surgical workspace in which a distractor is used to separate vertebrae or other body parts. In a retractor, distractor, and camera system, the camera system and/or distractor are configured to provide releasable attachment of the camera system to the distractor, and also provide for rotation of the camera assembly relative to the distractor to allow for adjusting the aim of the camera viewing axis to obtain an image of the surgical workspace established by the retractor. Because the distractor is positioned in close proximity to the involved vertebrae, placement of the camera system on the distractor can provide a better view of the surgical workspace compared to placement on the retractor.

DETAILED DESCRIPTION OF THE INVENTIONS

Figure 1:
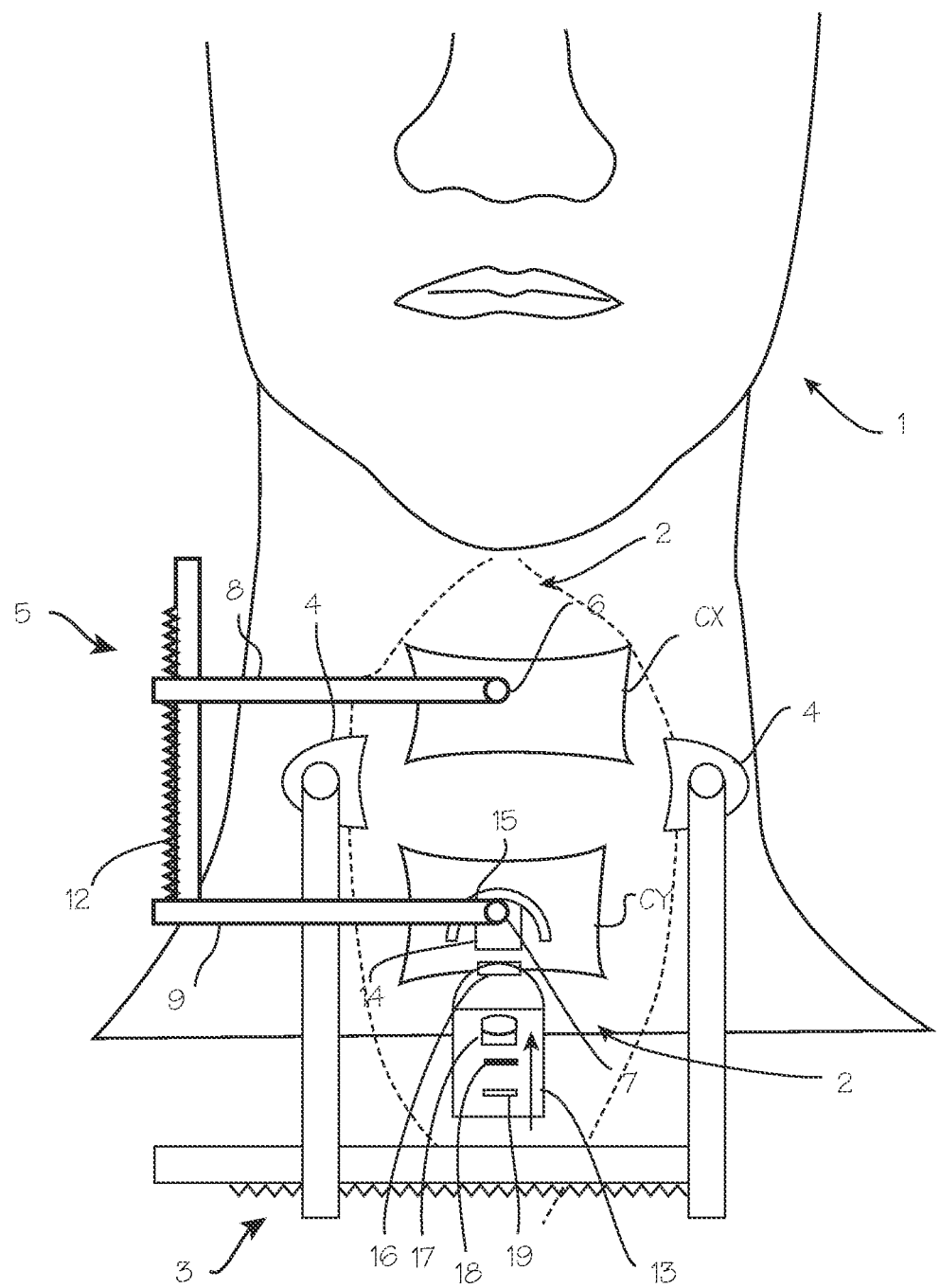
FIG. 1 illustrates the placement of a retractor, a distractor, and a camera system installed in the neck of a patient, in an anterior view.
Figure 2:
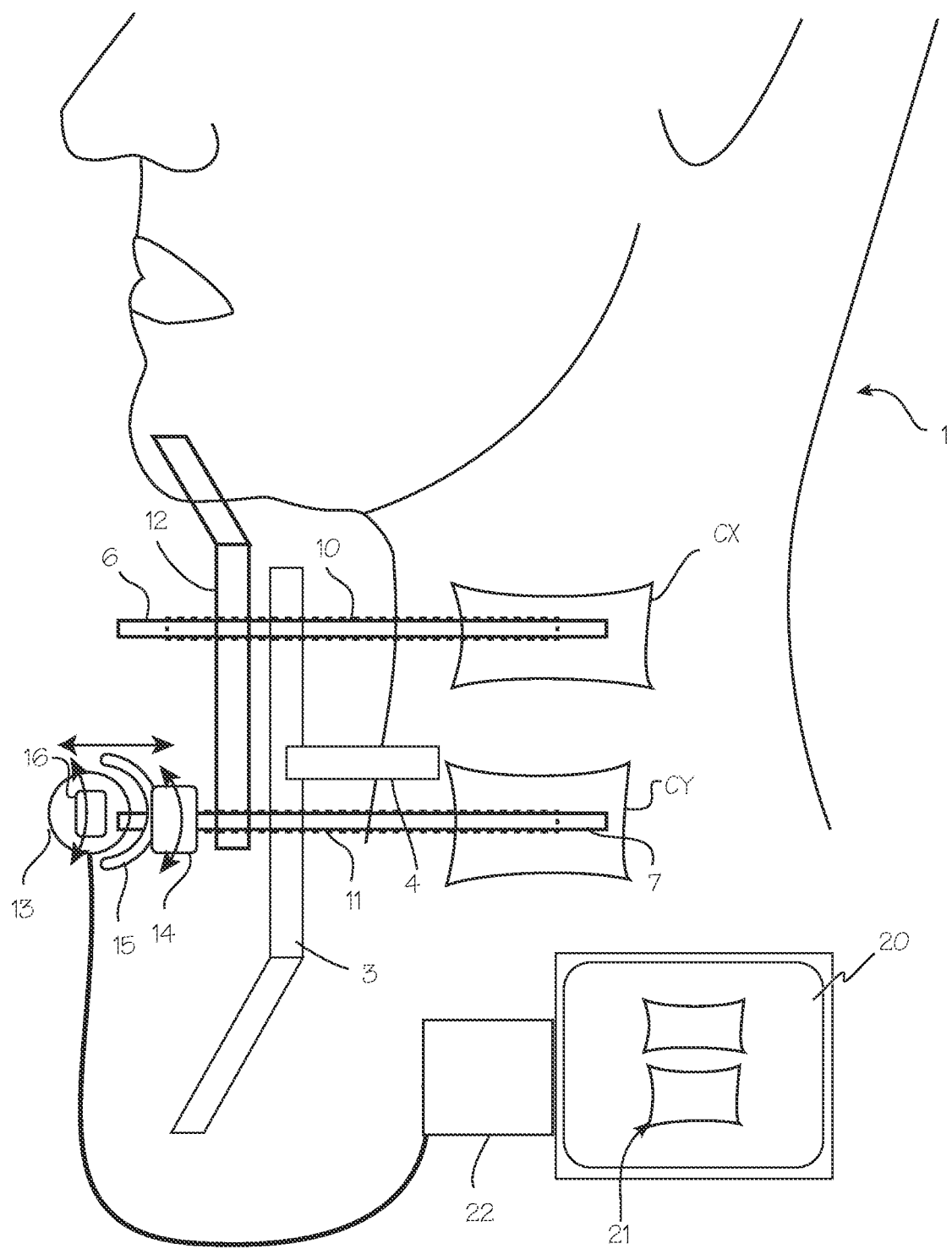
FIG. 2 illustrates the placement of a retractor, a distractor, and a camera system installed in the neck of a patient, in a lateral view.

FIGS. 1 and 2 illustrate the placement of a retractor, a distractor, and a camera system installed in the neck of a patient. The patient 1 has a surgical opening 2 the in the neck, exposing cervical vertebrae CX and CY (any pair of vertebrae C2 to C7). A retractor 3 is disposed in the surgical opening, with retractor blades 4 on either side of the opening. As illustrated, the retractor blades have been separated to retract skin and tissue obliquely to expose the vertebrae. A distractor 5 is disposed over the opening and the retractor, with distractor pins 6 and 7 (Caspar pins) fixed to separable distractor frame members 8 and 9 and to cervical vertebrae CX and CY, respectively. The Caspar pins may be fixed, in respect to the longitudinal axis of the patient, to the distractor frame members directly, or disposed within intervening tubes 10 or 11 (FIG. 2, in phantom) which are fixed to distractor frame members directly. The distractor is operable to translate the distractor pins 6 and 7, along distractor rail 12, away from each other, along the superior/inferior axis (the longitudinal axis) of the neck, when fixed to the cervical vertebrae CX and CY, to separate them. The distractor may be fixed, or not, to the retractor.

A camera assembly 13 is disposed on the distractor. Preferably the camera assembly is secured to the distractor through a mounting device that includes a means for releasably securing the camera assembly to the distractor. The camera assembly may be secured to the distractor via any distractor component, and may be secured to the distractor frame (frame members 8 or 9, or rail 12) or to one of the distractor pins 6 or 7 or distractor pin tubes 10 or 11. The means for releasably securing the camera assembly may comprise a magnet 14 secured permanently or releasably secured to the camera assembly, for example, where the distractor components are ferromagnetic, or it may comprise a spring clip, small clamp, etc. fixed to the camera assembly and configured to grasp the frame members 8 or 9, or rail 12 or one of the distractor pins 6 or 7 or distractor pin tubes 10 or 11. For attachment to the distractor pins 6 or 7 or distractor pin tubes 10 or 11, the means for releasably securing the camera assembly may comprise a bore passing through a portion of the camera assembly, configured to receive a proximal portion of a pin or pin tube, or a threaded tripod mount on the camera assembly paired with a threaded proximal portion of a pin or pin tube. Each distractor pin or distractor tube may comprises means for releasably securing the camera assembly to the distractor, whereby the camera assembly may be releasably secured to and subsequently released from one distractor pin or distractor pin tube and subsequently releasably secured to another distractor pin or distractor pin tube.

Figure 3:
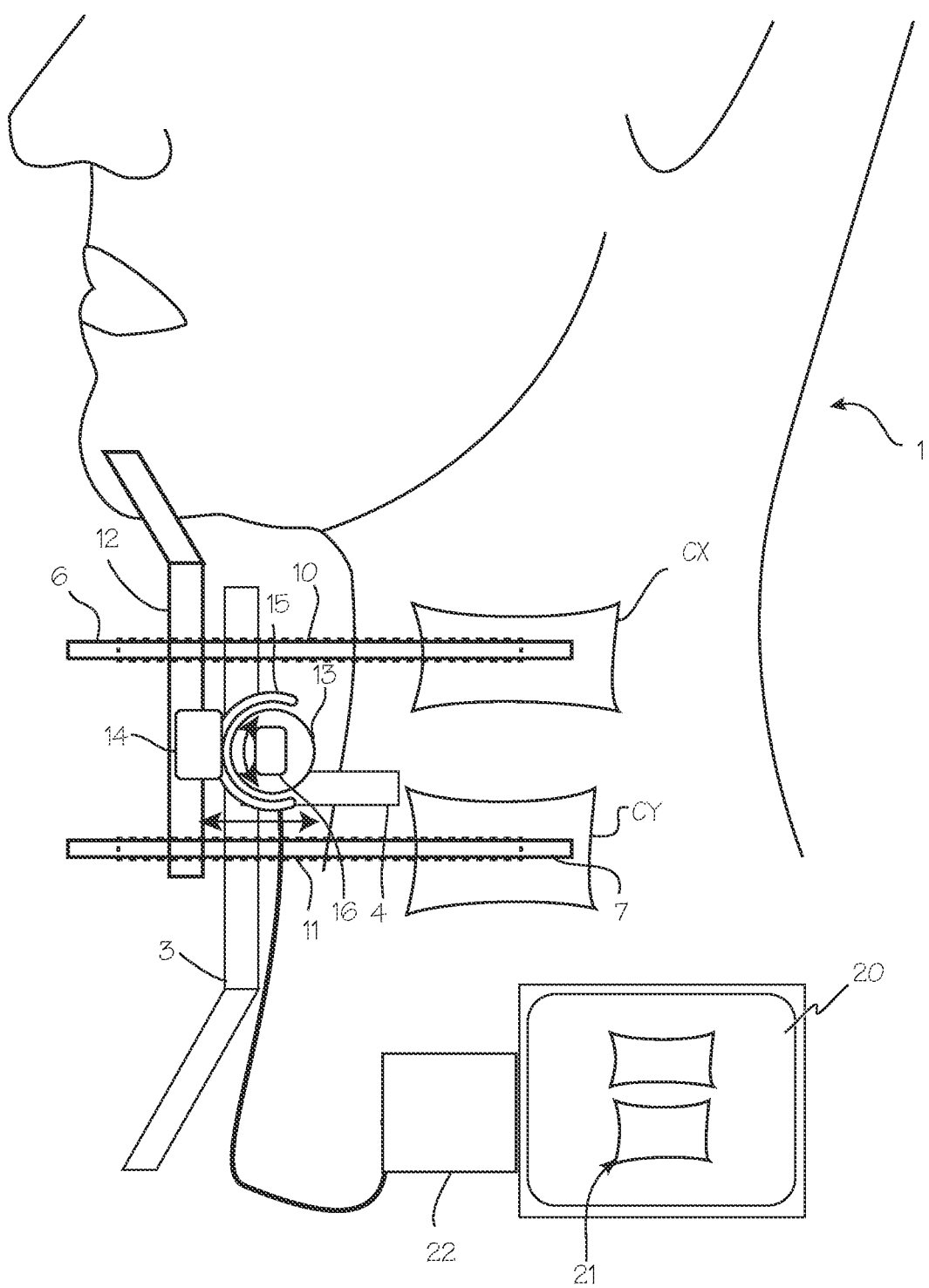
FIG. 3 illustrates the placement of a retractor, a distractor, and a camera system installed at the neck of a patient, in a lateral view, with the camera system secured to a posterior surface of the distractor.

FIG. 3 illustrates the placement of a retractor, a distractor, and a camera system installed at the neck of a patient, as in FIG. 2, with the camera system secured to a posterior surface, or underside, of the distractor. The camera system is releasably secured to the posterior surface of one of the distractor frame members, but may also be secured to a posterior surface of the distractor rail, or a portion of a distractor pin or distractor pin tube which is posterior to the distractor frame, between the distractor frame and the surgical opening.

The mounting device also includes a means for rotationally securing the camera assembly to the distractor (or, comparably, means for rotationally securing the camera assembly to the means for releasably securing the camera assembly). This may comprise a socket or cup 15, configured to receive a portion of the camera assembly 13. In the illustrated configuration, the cup is a partial hollow sphere configured to receive a spherical portion of the camera assembly, and the camera assembly includes housing or a distal/objective housing portion that is spherical, or has a body to distal/objective housing portion or other surface which is at least partially spherical and which is configured to snap-fit or friction fit into the spherical hollow of the socket or cup, allowing rotation of the camera assembly within the socket or cup to aim the camera assembly viewing axis into the surgical workspace opened by the retractor or the distractor. The spherical hollow need not comprise an entire sphere, so long as it is of partially spherical and of sufficient extent to positively capture the partially spherical portion of the camera housing. The cup may comprise a resilient material, chosen to easily expand to accept the distal/objective housing portion and thereafter close upon the distal/objective housing portion to provide a secure, rotatable coupling. The resilient cup, or fingers or extensions of the resilient cup, would thus comprise a portion that covers more than a hemisphere, to positively hold the camera assembly or the distal/objective housing portion or surface. The camera assembly may instead be rotationally fixed to the socket or cup that is configured to accept the distal/objective housing portion or surface (for example, a hexagonal camera head and corresponding hexagonal socket), and the socket or cup may be connected to the releasable attachment means with a rotatable joint, such as a ball-and-socket joint, lockable ball head or a living hinge. In either case, additional rotational joints may be provided between the distractor and the camera assembly, and additional magnetic or mechanical joints may be provided between the distractor and the camera. The camera mount maintains the camera assembly low to the surgical opening and located out of the instrument path created by the retractor and distractor. The camera mount may also be slidably fixed to the frame members or rail, and may be translatable along the rail and/or rotatable relative to the rail. With the camera assembly installed in the camera mount, the camera assembly may be rotatable laterally and tilted relative to the line of sight into the surgical opening to view the surgical field, maximizing the view with limited incisional opening and tissue exposure.

The camera assembly 13 preferably comprises a prism or reflector 16, a lens or lenses 17, the imaging device 18 and the control system 19 (if provided in the camera component of the system). The lens 17 may be part of an optical assembly that includes additional optical components. The imaging device 18 may be any suitable image sensor such as a CCD sensor or CMOS sensor. The control system 19 may include a controller, image processing components, data processing components and transmitters such as a controller and a transmitter to control the camera assembly and transmit data from the camera assembly (the data output system may be located off the device). Suitable cables or wireless transmitters may be used to connect the camera assembly to a display system and a power supply. The imaging sensor is characterized by an imaging plane, and the prism is aligned with the imaging plane to direct light directed parallel to the imaging plane toward the imaging plane. The prism/reflector is disposed along a line perpendicular to the imaging plane, and is oriented to direct light from the surgical field at the distal end of the surgical channel onto the imaging plane. The distal most optical surface of the camera assembly is maintained just proximal to the surgical opening, preferably proximal to the distractor frame, yet fixed to the distractor. Lighting for the workspace may be provided by LED's or other light sources fixed to the camera assembly or camera mount, which may be powered through the power source used for the camera assembly. The light sources and any associated cabling are thus maintained outside and above the opening and surgical channel established by the retractor and distractor, and do not extend past the retractor frame, as is required by current fiber optic bundles inserted through channels in the retractor blades (though additional lighting components may be placed into the surgical workspace, coupled to the distractor pin).

The camera assembly provides video images to a monitor 20. Image data from camera assembly 13 is transmitted to the monitor 20 to provide an image or images 21 of the structures at the surgical workspace at the distal end of the retractor blades and Caspar pins. The display may be operated by a control system 22 which is operable to receive image data from the camera assembly, transmit the image data to the display. A surgeon performing a procedure within the workspace can view images of the cervical vertebrae and other tissue, and tool tips and implants and other devices within the workspace, on the monitor to obtain additional and better visualization than might be obtained by direct vision looking down the retracted opening.

Thus, the system described above provides for visualization of a surgical workspace and includes a distractor, including separable distractor frame members and distractor pins configured for fixation to the distractor frame member and cervical vertebrae, where the distractor pins are fixable to the distractor frame members directly, or disposed within distractor tubes which are fixed to distractor frame members directly. The distractor is operable to translate the distractor pins, along a distractor rail, away from each other, along the superior/inferior axis of the neck, (for example for cervical spine surgery). The camera assembly includes means for rotationally securing the camera assembly and means for releasably securing the camera assembly to the distractor, to a distractor frame member, distractor pin or a distractor tube, so that the camera assembly can be easily fixed to the distractor before or after the distractor is installed and operated to distract tissue, so that the camera assembly can easily be adjusted to aim the viewing axis of the camera toward a desired point in the surgical workspace. The camera may be rotatably secured to a distractor pin (or tube), so that is may be rotated about the distractor pin (or tube) to provide a a view of the surgical workspace from various angles.

In use, a surgeon may install a retractor in the neck of a patient to retract tissue away from the cervical vertebrae, and install Caspar pins into adjacent vertebrae, fix the distractor to the Caspar pins and operate the distractor to spread the pins and thereby distract the vertebrae apart, in order to perform a procedure such as an interbody fusion, anterior cervical discectomy or other procedure. The surgeon may attach the camera mount and camera assembly to the distractor frame members or Caspar pins, rotate the camera assembly within the camera mount, or rotate rotatable joints of the camera mount, to direct the field of view of the camera assembly toward the surgical workspace at the distal end of the retractor blades, such as the cervical vertebrae and surrounding tissue, tool tips inserted into the workspace, and implants inserted into the workspace.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method of performing surgery on a spine of a patient comprising the steps of:

creating a surgical opening along an incision in the front of the neck of the patient to expose a first and second vertebrae of the patient by installing a retractor with retractor blades operable to retract tissue along the incision and operating the retractor to retract tissue away from the first and second vertebrae to create the surgical workspace;

providing a distractor, comprising separable distractor frame members and distractor pins configured for fixation to said distractor frame member and cervical vertebrae;

securing the distractor to the first vertebrae and the second vertebrae by installing the distractor pins fixable, in respect to a longitudinal axis of the patient, to the distractor frame members directly, or disposed within distractor tubes which are fixed to distractor frame members directly;

operating the distractor to distract the first vertebrae away from the second vertebrae by translating the distractor pins, along a distractor rail, away from each other, along the superior/inferior axis (the longitudinal axis) of the neck;

releasably securing a camera assembly and a socket to the distractor, to a distractor frame member, distractor pin, a distractor tube or a distractor rail, the socket made of a resilient material and comprising fingers extending from the socket to encompass a portion of the camera assembly and configured to rotationally receive a portion of the camera assembly which is at least partially spherical and configured to fit into a spherical hollow of the socket; and operating the camera assembly to obtain images of the surgical workspace.

2. The method of claim 1 further comprising the steps of:
providing a distractor component that is ferromagnetic and providing a socket that is a magnet secured to the camera assembly.

3. The method of claim 1 further comprising the steps of:
releasably securing the camera assembly to a posterior surface of a distractor frame member, a posterior surface of the distractor rail, or a portion of a distractor pin or distractor pin tube which is posterior to the distractor frame, between the distractor frame and the surgical opening.

4. The method of claim 1 further comprising the steps of:
releasably securing and subsequently releasing the camera assembly from one distractor pin or distractor pin tube and subsequently releasably securing to another distractor pin or distractor pin tube.

5. A method of performing surgery on a spine of a patient comprising the steps of:

creating a surgical opening along an incision in the front of the neck of the patient to expose a first and second vertebrae of the patient by installing a retractor with retractor blades operable to retract tissue along the incision and operating the retractor to retract tissue away from the first and second vertebrae to create the surgical workspace;

providing a distractor, comprising separable distractor frame members and distractor pins configured for fixation to said distractor frame member and cervical vertebrae;

securing the distractor to the first vertebrae and the second vertebrae by installing the distractor pins fixable, in respect to a longitudinal axis of the patient, to the distractor frame members directly, or disposed within distractor tubes which are fixed to distractor frame members directly;

operating the distractor to distract the first vertebrae away from the second vertebrae by translating the distractor pins, along a distractor rail, away from each other, along the superior/inferior axis (the longitudinal axis) of the neck;

releasably securing a camera assembly and a cup with a partial spherical hollow to the distractor, to a distractor frame member, distractor pin, a distractor tube or a distractor rail, the cup made of a resilient material and said partial spherical hollow configured to receive a spherical portion of the camera assembly; and operating the camera assembly to obtain images of the surgical workspace.

6. The method of claim 5 further comprising the steps of:
providing a distractor component that is ferromagnetic and providing a socket that is a magnet secured to the camera assembly.

7. The method of claim 5 further comprising the steps of:
releasably securing the camera system to a posterior surface of a distractor frame member, a posterior surface of the distractor rail, or a portion of a distractor pin or distractor pin tube which is posterior to the distractor frame, between the distractor frame and the surgical opening.

8. The method of claim 5 further comprising the steps of:
Releasably securing and subsequently releasing the camera assembly from one distractor pin or distractor pin tube and subsequently releasably securing to another distractor pin or distractor pin tube.

\* \* \* \* \*